(12) United States Patent
Wicker et al.

(10) Patent No.: US 7,780,897 B2
(45) Date of Patent: Aug. 24, 2010

(54) HYDROGEL CONSTRUCTS USING STEREOLITHOGRAPHY

(75) Inventors: Ryan Wicker, El Paso, TX (US); Francisco Medina, El Paso, TX (US); Karina Arcaute, El Paso, TX (US); Luis Ochoa, El Paso, TX (US); Christopher Elkins, Redwood City, CA (US); Brenda Mann, Salt Lake City, UT (US)

(73) Assignees: Board of Regents, The University of Texas System, Austin, TX (US); Keck Graduate Institute, Claremont, CA (US)

( * ) Notice: Subject to any disclaimer, the term of this patent is extended or adjusted under 35 U.S.C. 154(b) by 1354 days.

(21) Appl. No.: 10/907,984

(22) Filed: Apr. 22, 2005

(65) Prior Publication Data

US 2006/0237880 A1    Oct. 26, 2006

(51) Int. Cl.
*B29C 35/08* (2006.01)
*B29C 71/00* (2006.01)
(52) U.S. Cl. .................. 264/401; 264/233; 264/236
(58) Field of Classification Search ............. 264/233, 264/236, 401
See application file for complete search history.

(56) References Cited

U.S. PATENT DOCUMENTS

| | | | |
|---|---|---|---|
| 4,575,330 A | 3/1986 | Hull | |
| 4,942,001 A * | 7/1990 | Murphy et al. | 264/401 |
| 5,088,047 A | 2/1992 | Bynum | |
| 5,143,663 A | 9/1992 | Leyden et al. | 264/22 |
| 5,398,193 A | 3/1995 | deAngelis | |
| 5,402,351 A | 3/1995 | Batchelder et al. | 364/468 |
| 5,510,066 A | 4/1996 | Fink et al. | |
| 5,658,412 A | 8/1997 | Retallick et al. | 156/272.8 |
| 5,779,967 A | 7/1998 | Hull | 264/401 |
| 5,786,023 A | 7/1998 | Maxwell et al. | |
| 5,876,550 A | 3/1999 | Feygin et al. | 156/264 |
| 5,902,538 A | 5/1999 | Kruger et al. | |

(Continued)

FOREIGN PATENT DOCUMENTS

DE    29907262    8/1999

(Continued)

OTHER PUBLICATIONS

Office Action issued in U.S. Appl. No. 10/903,379, mailed Mar. 27, 2008.

(Continued)

*Primary Examiner*—Leo B Tentoni
(74) *Attorney, Agent, or Firm*—Fulbright & Jaworski (57) ABSTRACT

A preferred embodiment of the present invention provides a method and system for building cost-efficient biocompatible hydrogel constructs using stereolithography. Hydrogel constructs may be used in, for example, multi-lumen nerve regeneration conduits and other tissue engineering scaffolds with embedded channel architecture that facilitate tissue regeneration through possible incorporation of precisely located bioactive agents, cells, and other desired inert and/or active chemical agents and devices. Another preferred embodiment of the present invention provides a method of fabricating a hydrogel construct comprising: solidifying a first solution into a first construct layer with a first energy dosage using stereolithography, the first solution comprising: a first polymer; and a first photoinitiator, wherein the first polymer and first photoinitiator are of a first concentration.

25 Claims, 11 Drawing Sheets

U.S. PATENT DOCUMENTS

| | | | |
|---|---|---|---|
| 6,027,699 | A | 2/2000 | Holcomb et al. |
| 6,153,034 | A | 11/2000 | Lipsker |
| 6,158,346 | A | 12/2000 | Zhang |
| 6,159,411 | A | 12/2000 | Kulkarni et al. |
| 6,179,601 | B1 | 1/2001 | Kruger et al. |
| 6,206,672 | B1 | 3/2001 | Grenda |
| 6,216,765 | B1 | 4/2001 | Tseng et al. |
| 6,242,163 | B1 | 6/2001 | Stampfl et al. |
| 6,309,581 | B1 | 10/2001 | Gervasi |
| 6,372,178 | B1 | 4/2002 | Tseng .................... 264/656 |
| 6,391,251 | B1 | 5/2002 | Keicher et al. |
| 6,450,393 | B1 | 9/2002 | Doumanidis et al. |
| 6,492,651 | B2 | 12/2002 | Kerekes .................. 250/559.2 |
| 6,549,710 | B2 | 4/2003 | Simmons et al. ............ 385/121 |
| 6,623,687 | B1 | 9/2003 | Gervasi et al. |
| 6,630,093 | B1 | 10/2003 | Jones |
| 6,641,897 | B2 | 11/2003 | Gervasi |
| 6,656,410 | B2 | 12/2003 | Hull et al. ................. 264/401 |
| 6,706,234 | B2 | 3/2004 | Huang .................... 264/435 |
| 6,752,948 | B2 | 6/2004 | Newell et al. .............. 264/234 |
| 6,847,774 | B2 | 1/2005 | Simmons et al. ............ 385/134 |
| 6,849,223 | B2 | 2/2005 | Dean et al. |
| 7,229,144 | B2 | 6/2007 | Nielsen et al. ................. 347/2 |
| 7,419,630 | B2 | 9/2008 | Palmer et al. .............. 264/401 |
| 2001/0026793 | A1* | 10/2001 | Jamiolkowski et al. ... 424/78.17 |
| 2002/0171178 | A1 | 11/2002 | Dean et al. |
| 2003/0032733 | A1 | 2/2003 | Fisher et al. |
| 2004/0006438 | A1 | 1/2004 | Hastert et al. |
| 2004/0020614 | A1 | 2/2004 | Lindsay et al. |
| 2004/0120981 | A1* | 6/2004 | Nathan ...................... 424/426 |
| 2005/0169962 | A1* | 8/2005 | Bhatia et al. ............... 424/423 |
| 2005/0263932 | A1 | 12/2005 | Heugel ...................... 264/497 |

FOREIGN PATENT DOCUMENTS

| | | |
|---|---|---|
| EP | 1245369 | 2/2002 |
| WO | WO 02/085246 | 10/2002 |
| WO | WO 03//002490 | 1/2003 |
| WO | WO 2004006840 A2 * | 1/2004 |

OTHER PUBLICATIONS

Office Action issued in U.S. Appl. No. 10/903,379, mailed Oct. 1, 2008.

Office Action issued in U.S. Appl. No. 11/095,120, mailed Aug. 1, 2008.

Office Action issued in U.S. Appl. No. 11/095,120, mailed Nov. 5, 2008.

U.S. Appl. No. 12/181,486 entitled "Methods and Systems for Rapid Prototyping of High Density Circuits," by Jeremy A. Palmer et al., filed Jul. 29, 2008.

Office Communication issued in related U.S. Appl. No. 11/095,120, dated Jun. 22, 2009.

Baldwin, Samuel P. et al; "Materials For Protien Delivery in Tissue Engineering", Advanced Drug Delivery Reviews 33, 1998 Elsevier Science B.V., p. 71-86.

Kataria Alok et al; "Building Around Inserts: Methods For Fabricating Complex Devices In Stereolithography" DETC00/MECH-14206; 2000 ASME, p. 1-11.

Maruo Shoji et al; Multi-Polymer Microstereolithography For Hybrid Opto-Mems; Department of Micro System Engineering, Nagoya University, 2001 IEEE, p. 151-154.

Lee Jim H. et al; "Cure Depth In Photopolymerization: Experiments and Theory", J. Mater. Res., vol. 16, No. 12, Dec. 2001; p. 3536-3544; 2001 Materials Research Society.

Hoffman Allan S.; "Hydrogels For Biomedical Applications", Advanced Drug Delivery Reviews 43 (2002); 2002 Elsevier Science B.V., Jul. 26, 2001, p. 3-12.

Cooke Malcolm N. et al; "Use of Stereolithography to Manufacture Critical-Sized 3D Biodegradable Scaffolds for Bone Ingrowth" 2002 Wiley Periodicals, Inc., Oct. 2001.

Liu Valerie A. et al; "Three Dimensional Photopatterning of Hydrogels Containing Living Cells", Hybrid Bio/Artificial Microdevices, Biomedical Microdevices 4:4; 2002 p. 257-26.

De Laurentis Kathryn J. et al; "Procedure For Rapid Fabrication Of Non-Assembly Mechanisms With Embedded Components" DETC 2002/MECH-34350; 2000 ASME, p. 1-7.

Hatanaka Motohide et al; "Process Planning for Embdding Flexible Materials in Multi-material Prototypes" DETC2003/DFM048166, 2003 ASME, p. 1-9.

Drury Jeanie L. et al; "Hydrogels For Tissue Engineering: Scaffold Design Variables and Applications", Science Direct, Biomaterials, 2003 Elsevier Ltd., p. 1-15.

Geving Brad et al; "Conceptual Design Of A Generalized Stereolithography Machine", The George W. Woodruff School of Mechanical Engineering, pp. 1-8.

De Laurentis Kathryn J. et al; "Rapid Fabrication of Non-Assembly Robotic Systems With Embedded Components", Robotics and Mechatronics Laboratory; Rutgers University, pp. 1-30, (2002).

Dhariwala, Busaina et al, Rapid Prototyping of Tissue-Engineering Constructs, Using Photopolymerizable Hydrogels and Stereolithography, Tissue Engineering, vol. 10 (9/10), pp. 1316-1322, (2004).

Heath, Carole A. et al; The Development of Bioartificial Nerve Grafts for Peripheral-nerve Regeneration; TibTech, vol. 16, pp. 163-168, Apr. 1999.

Sundback, Cathryn et al; Manufacture of Porous Polymer Nerve Conduits by a Novel Low-Pressure Injection Molding Process, Biomaterials, vol. 23, pp. 819-830 (2003).

Hadlock, Tessa, et al; A Polymer Foam Conduit Seeded with Schwann Cells Promotes Guided Peripheral Nerve Regeneration, Tissue Engineering, vol. 6(2), pp. 119-127 (2000).

Cooke, Malcolm, et al; Use of Stereolithography to Manufacture Critical-Sized 3D Biodegradable Scaffolds for Bone Growth, J. Biomed Mater Res Part B: Appl. Biomater 64B: 65-69.

* cited by examiner

HYDROGEL CONSTRUCTS USING STEREOLITHOGRAPHY

BACKGROUND

The present invention relates to the general field of rapid prototyping technology, and in particular, to stereolithography methods and systems.

Rapid prototyping (RP) technologies, also known as Solid Freeform Fabrication (SFF), layered manufacturing and other similar technologies enable the manufacture of complex three-dimensional (3D) parts. RP technologies, in particular, generally construct parts by building one layer at a time. RP technologies are commonly used to build parts and prototypes for use in, for example, the toy, automotive, aircraft and medical industries. Oftentimes prototypes made by RP technologies aid in research and development and provide a low cost alternative to traditional prototyping. In a few cases, RP technologies have been used in medical applications such as those associated with reconstructive surgery and tissue engineering (TE).

Stereolithography (SL) is one of the most widely used RP technologies known in the art. The resolution of SL machines and the ability of SL to manufacture highly complex 3D objects, make SL ideal for building both functional and non-functional prototypes. In particular, SL techniques provide an economical, physical model of objects quickly and prior to making more expensive finished parts. The models are readily customizable and changes may be easily implemented.

SL generally involves a multi-stage process. For example, the first stage involves designing and inputting a precise mathematical geometric description of the desired structure's shape into one of many computer-aided design (CAD) programs and saving the description in the standard transform language (STL) file format. In the second stage, the STL file is imported into SL machine-specific software (RP software). The RP software slices the design into layers and determines the placement of support structures to hold each cross-section in place while building the structure layer by layer. By computing build parameters, the RP software controls the part's fabrication. In the layer preparation stage, the build parameters for the desired part are translated into machine language. Finally, the machine language controls the SL machine to build a desired part and its support structure layer by layer. SL machines typically focus an ultraviolet (UV) laser onto a cross-section of a liquid photopolymer resin. The laser, in turn, selectively cures a resin to form a structure, such as anatomical shapes (i.e., organs and tissues), layer by layer. Ultimately, the part is cleaned, the support structure is removed and the part is post-cured (typically exposed to UV) prior to completion. The operator may, however, need to sand, file or use some other finishing technique on the part in order to provide a specific surface finish to the structure, which may include painting, plating and/or coating the structure's surface.

SL technologies known in the art generally include, for example, a laser, a liquid level sensing system, laser beam optics and controllable scanning mirror system, a vertically movable platform, a single resin retaining receptacle or vat and a recoating device. During the laser scanning phase, a series of optics and controllable scanning mirrors typically raster a UV laser beam to solidify a photocurable polymer resin. The subject 3D part is first attached to the platform by building a support structure with the platform in its topmost position. This step allows for misalignment between the platform and the surface of the liquid resin—once constructed, the base support structure is parallel with the surface of the liquid. When building the subject part simultaneously with its required support structure and after the laser beam completes a layer, the platform typically is vertically traversed downward a distance equal to the build layer thickness. After the platform is vertically traversed downward and prior to selectively curing the next layer, a recoating device is typically traversed horizontally across the part leaving a uniform layer of liquid polymer. The recoating device ensures that trapped spaces within the part are filled with liquid resin (which may be required for future build layers) and maintains a constant build layer thickness. The process repeats as each layer is built. Complex-shaped parts are thus manufactured by repeating the layering process. Once complete, the part is typically raised out of the liquid resin, the support structure is removed from the part, the part is cleaned and then post-cured. The operator may, however, need to sand, file or use some other finishing technique on the part in order to provide a specific surface finish to the structure, which may include painting, plating and/or coating the structure's surface.

Certain RP technologies facilitate the fabrication of parts used in medical applications. Such parts require additional design considerations. TE techniques, in particular, rely on the use of a scaffold, a framework that provides structural support for cells while those cells regenerate the tissue. These scaffolds may also provide signals to the cells to elicit particular desired behaviors. One of the most challenging problems in TE is providing adequate nutrition to cells seeded within implanted scaffolds. TE techniques known in the art have shown that the diffusion of oxygen and nutrients is not sufficient to sustain cell viability beyond distances of approximately 75 microns in the body. Accordingly, TE techniques must retain precise control over the resulting 3D geometry in order to design favorable diffusion into a scaffold and thus maintain cell viability. Although SL has the resolution and speed to make highly complex 3D structures economically, SL has not been used to aid in TE because SL resins known in the art are not certified for implantation in humans. Other systems known in the art for creating complex 3D TE scaffolds are time-consuming and complicated and therefore are not conducive to mass manufacturing. Accordingly, what is desired is a system and method of quickly building and mass producing biocompatible and implantable constructs with precise control over placement of scaffold materials and bioactive agents and cells to promote favorable tissue regeneration and nutrient diffusion within a scaffold in an economical manner possibly with SL technologies.

Hydrogels are currently being used for a number of different TE applications, particularly for soft tissues. Hydrogels are biocompatible materials with high water content and are suitable as scaffolding materials because of their similarity, both mechanically and structurally, to extracellular matrices. In addition, hydrogels exhibit favorable diffusion characteristics and are currently used in photolithographic processes using manual lithographic masking techniques as well as a variety of other processes. There are enumerable TE applications that can benefit from precisely manufacturing hydrogel constructs with bioactive agents and cells. Hydrogels, however, are not currently adequately supported by layered manufacturing (LM) technologies using SL.

Embedded channels may be important to build angiogenic structures or roadways between proliferative structures located within hydrogel scaffolds. Thus, biological and architectural cues need to be assessed to fabricate cytocompatible scaffolds. For example, gradients of growth factors have been found to direct cell migration and neurite extension, and ultimately enhance tissue regeneration in both guided angiogenesis and subsequent vasculogenesis in vivo and peripheral nerve regeneration. Several agents, such as vascular endothelial growth factor (VEGF), for example, exert potent angiogenic effects. In the case of VEGF, these effects are severalfold, ranging from marrow stimulation of endothelial precursor production and release to local selective recruitment of precursors and enhanced, for example, vascular permeability which in turn enhances vascular bud formation.

Once initiated, a vascular bud is potentially guided by gradients that allow permeability in the target bud direction and stabilization of the adjacent sides. Several stabilizing agents have been identified in vitro. These agents, such as angiopoietin 2, serve to prevent aberrant budding and to guide the bud in the direction of high permeability. When provided nonspecifically, these agents suppress bud formation. Thus, a gradient in VEGF will facilitate guided bud formation and propagation. A reverse gradient of angiopoietin 2 should stabilize directional control of angiogenesis and prevent nonspecific turns or termination. Further, extracellular matrix (ECM) elements have been shown to either facilitate (hyaluronic acid) or inhibit (polymerized collagen) directional angiogenesis through specific cellular receptors. Thus, what is desired is exogenously engineered gradients of biologic agents and/or ECM that will potentially facilitate induction and directional propagation of angiogenesis in an engineered implantable, cytocompatible scaffold.

One particular need in the art is a system and method to create complex nerve guidance conduits. Currently, peripheral nerve repair is accomplished by using a nerve autograft. Autografting involves taking a portion of a nerve from one location in the body (a donor site) and placing it in another part of the body exhibiting a specified need. There are several drawbacks to autografting including, for example, requiring multiple surgical sites and a considerable risk of neuroma formation at the donor site. Oftentimes, results from autografting have been variable and more often altogether unsuccessful.

Nerve guidance conduits (NGCs) offer a promising alternative to autografting. NGCs are tubes that are sutured to nerve stumps to bridge the gap and aid in guiding sprouting axons from the regenerating nerve toward their target. NGCs retain neurotrophic factors and other compounds secreted by the damaged nerve, thus aiding in regeneration and preventing the infiltration of fibrous tissue. There are currently two types of NGCs available, one made of collagen and the other made of polyvinylalcohol (a hydrogel). These NGCs, however, are simple, single material and single lumen conduits that fail to recreate the 3D structure of the nerve.

Multi-lumen conduits are desirable because they mimic the natural peripheral nerve structure and increase surface area for neurite attachment/extension and support cell attachment/migration. Multi-lumen conduits thus allow for more precisely located growth factors and support cells within a tissue scaffold. Although multi-lumen conduits made with poly(lactic-co-glycolic acid) have previously been made, the techniques used to make such scaffolds are difficult to scale-up to a manufacturing level, do not allow for cells to be homogeneously seeded within the conduit during its manufacture, and do not allow the mechanical properties of and bioagents within the construct to vary throughout the construct, which is afforded by layered manufacturing.

Thus, systems known in the art fail to mass produce complex, multiple material 3D constructs with embedded channel architecture from hydrogels using SL technology. Accordingly, what is desired is a low cost, efficient and easy-to-use system which has the ability to fabricate hydrogel constructs with embedded channels of virtually any orientation. What is further desired is a system which enables scaffold fabrication with internal channel architecture including any variable channel orientation. What is still further desired is the ability to fabricate multiple material hydrogel constructs that enable the construction of precise scaffolds with variable hydrogel scaffold materials both within and across layers.

In addition, what is still desired is the ability to fabricate multiple material hydrogel constructs with precisely placed bioactive agents and cells both within and across layers. What is further desired is a simple method for manufacturing multi-lumen conduits of bioactive hydrogels as potential scaffolds for peripheral nerve regeneration. What is still further desired is a simple method for manufacturing complex bioactive hydrogel constructs as potential scaffolds for guided angiogenesis and adipose tissue generation. What is also still further desired is a simple method for fabricating multi-material constructs that may serve as TE scaffolds.

SUMMARY OF THE INVENTION

One aspect of the present invention overcomes the aforementioned limitations in an effective and efficient manner, thus expanding the use of RP in various applications and improves SL functionality. In another aspect, the present invention will accommodate these needs and provide further improvements in TE, chemical sensing, biological sensing and numerous other applications requiring complex, three-dimensional, multi-material, multi-element and/or multi-color, biocompatible manufacturing. In still another aspect, the present invention provides a multi-material SL system that builds angiogenic structures or roadways between proliferative structures for use in, for example, guided angiogenesis to restore vascular function. In yet another aspect, the present invention provides a SL system for constructing bioactive, multi-lumen nerve guidance conduits. In still another aspect, the present invention provides a system for fabricating tissue scaffolds such as, for example, tissue scaffolds for promoting adipose tissue population and growth.

BRIEF DESCRIPTION OF THE DRAWINGS

The above and further advantages of the invention may be better understood by referring to the following description in conjunction with the accompanying drawings, in which:

FIG. 2A depicts the chemical composition of a preferred hydrogel used in an aspect of the present invention;

FIGS. 2B and C depict the preferred chemical compositions preferred photoinitiators used in an aspect of the present invention;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Figure 1:
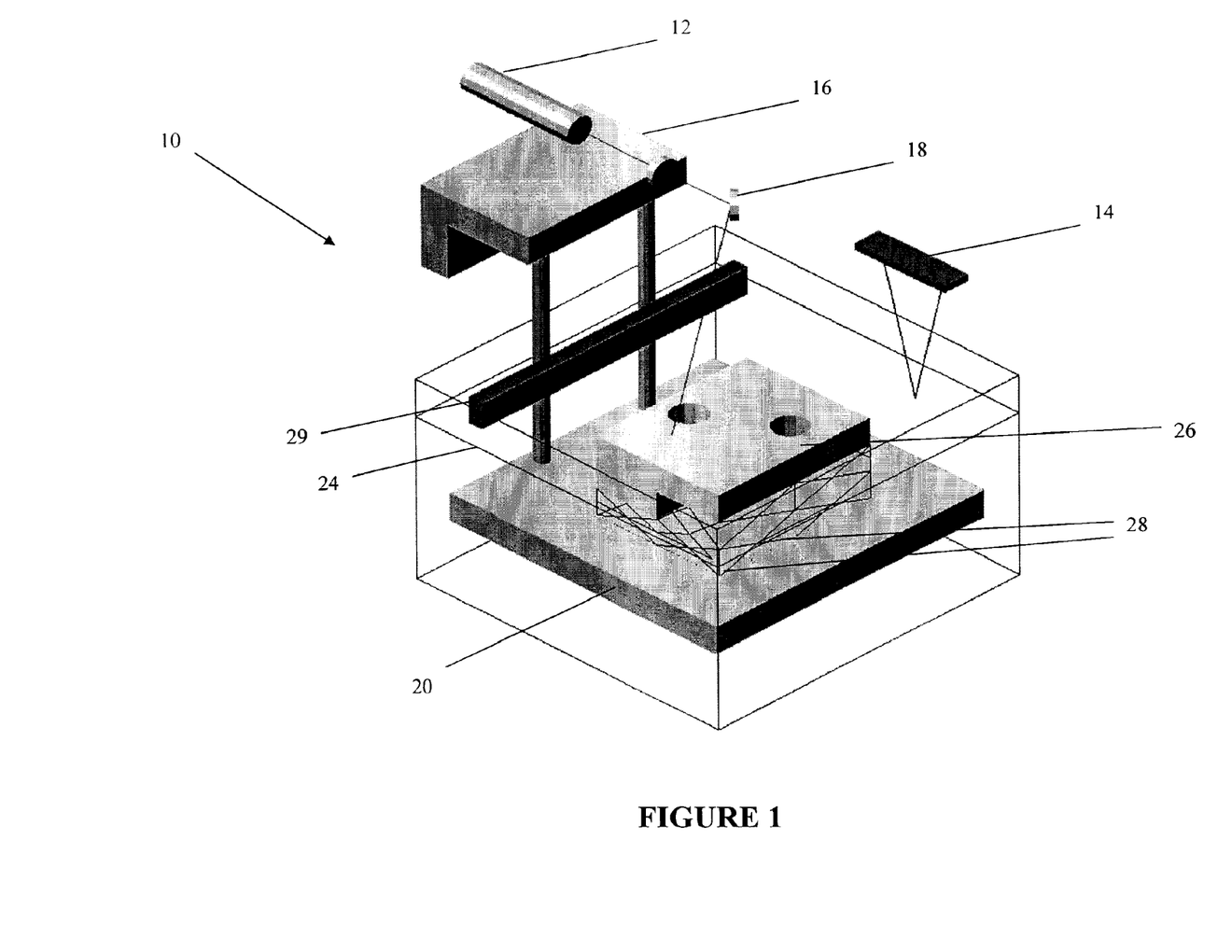
FIG. 1 is a schematic of a typical SL machine known in the art.

A typical prior art SL machine 10, as illustrated in FIG. 1, generally includes a UV laser beam 12, a liquid level sensing system 14, optics 16 and controllable scanning mirror system 18, a vertically movable platform 20 and a resin retaining receptacle or vat 22. The vat 22 houses, for example, a liquid photocurable polymer resin 24 and, generally, the SL machine 10 rasters a UV laser beam 12 across the resin through a series of optics 16 and a controllable scanning mirror system 18. In most designs, the subject three-dimensional (3D) part 26 is usually first attached to the platform 20 by building a base support structure 28 while the platform 20 is still in its topmost position. The support structure 28 is usually made up of fine filaments that support the subject part's 26 overhangs and are manufactured simultaneously using the same resin 24. Prior art designs typically incorporate a recoating device, recoating blade or other sweeping device 29 that sweeps or horizontally translates across the surface of the liquid after the platform 20 and subject part 26 have been traversed downward a distance equal to the build layer thickness. Thus, the recoating device 29 facilitates uniform liquid layers on the surface of the subject part 26 and eliminates trapped gases or bubbles and/or trapped volumes left on or underneath the platform 20 and/or the subject part 26 both before and during the building process.

Referring still to the prior art SL machine 10 depicted in FIG. 1, after the SL machine 10 rasters the UV laser beam 12 and completes a given layer (which also includes waiting a sufficient time for the reaction to finish after the laser beam has completed its scan), the platform 20 is vertically traversed downward a distance equal to the build layer thickness typically between but not limited to 2 and 6 mils or optionally traversed downward a distance greater than the build layer thickness in order to dip the subject part 26 into the resin 24 and fill any internal part cavities. Once dipping the subject part 26 is completed, if dipping is optionally performed, the platform 20 is then traversed upward until the top of the subject part attached to the platform is located a distance equal to the build layer thickness from the surface of the resin 24. The build layer thickness usually depends on the type of build desired. Prior to beginning a new reaction with the laser 12, a recoating device 29 typically traverses the liquid resin 24 surface as described previously, and the SL machine 10 waits a prescribed amount of time for the liquid resin to reach a state of equilibrium (so that essentially all waves and any other movement of the liquid resin has stopped) prior to starting the next layer. The process repeats as each layer is built. The materials used within the layer may be varied in a number of different configurations including, for example, the materials used to manufacture the layers can be varied both within and across the layers. Complex-shaped parts are thus manufactured by repeating the layering process. Once complete, the subject part 26 is typically raised out of the liquid polymer resin 24, the support structures 28 are removed and the subject part 26 is cleaned (preferably with a typical cleaning solution or a cytocompatible solution) and post-cured, usually in a UV oven (not shown). However, it should be understood that support structures 28 may be removed before, during, and/or after the cleaning and curing/drying processes.

In order to attach newly formed layers to previously cured layers, it is crucial to maintain a certain liquid photocurable resin 24 chemistry, layer thickness and laser energy so that the laser 12 is capable of curing beyond the layer thickness into previously cured layers (also known as "laser overcure"). Cure depth, a fundamental characteristic of liquid photocurable resins 24, measures the penetration depth of a laser at which the laser successfully cures the liquid photocurable resin 24 for a given laser energy. As described earlier, in a typical commercial SL machine 10 a series of optics 16 focuses and directs the laser 12 onto the liquid surface while the scanning mirrors 18 controls the laser's movement in the X-Y plane across the vat 22. Because commercial SL machines 10 accommodate a dynamic scanning mirror system, photochemical reactions are controlled by varying the scan speed of the laser 12 (for a fixed laser power). Thus, understanding and characterizing the cure depth behavior of the liquid photocurable resins 24 is necessary for successfully fabricating 3D objects using SL and its scanning mirror system 18 as seen, for example, in the later-described example.

Additionally, in order to successfully fabricate embedded channels and features that are opened or closed in and/or between cured layers, for example, the particular characteristics of the hydrogel solution (e.g., a photoinitiator (PI), poly(ethylene glycol) (PEG) and distilled water solution) need to be characterized. Certain unique characteristics must be exhibited in order to allow for successful fabrication. For example, some hydrogel solutions exhibit characteristics, such as hydrogel thickness or cure depth, that may potentially vary widely as a function of Pi type and concentration, energy dosage and polymer concentration in the hydrogel solution as also demonstrated in the later-described example.

Polymers that may be used in the present invention include any number of polymers with photoreactive functional groups and are capable of forming a hydrogel construct. These polymers include natural, synthetic, and semi-synthetic polymers known to those of skill in the art, and may be degradable or non-degradable. One exemplary polymer is derivatized PEG having functional groups such as acrylate, methacrylate, or vinyl sulfone. The PEG may have a molecular weight between about 1000 and 20,000, preferably between about 1000 and 10,000. The PEG may be a straight linear chain with a functional group on either end, such as PEG diacrylate, or may be a multi-armed PEG. Other polymers which may be used include, for example, derivatized polyvinyl alcohol, hyaluronic acid, chondroitin sulfate, and collagen. For example, methacrylated hyaluronic acid and methacrylated chondroitin sulfate have both been photocrosslinked into hydrogels. Other useful polymers capable of forming hydrogels following photocrosslinking are well-known to those of skill in the art. The concentration of the polymer in solution is preferably between about 1% and 30% (w/v).

Various biocompatible fluids may be used in conjunction with aspects of the present invention, including water, buffer (such as phosphate-buffered saline) and cell culture media. When cells or bioactive factors are included in the polymer solution, the fluid is preferably at a pH of about 7.0 to 7.8, most preferably about 7.4.

Various PIs may be used in conjunction with a preferred embodiment of the present invention and are generally known to those of skill in the art of photocrosslinking. The PI preferably has an absorption in the UV wavelength range, and more preferably in the long UV wavelength range. Preferred PIs, include but are not limited to, 2,2-dimethyl-2-phenylacetophenone, 2-hydroxy-2-methyl-1phenyl-1-propanone (HMPP), and 2-hydroxy-1-[4-(2-hydroxyethoxy)phenyl]-2-methyl-1-propanone (Irgacure 2959, Ciba-Geigy). The concentration of the PI in the polymer solution is preferably below about 5%, and more preferably below about 1%, particularly when cells are present in the polymer solution. It should be understood by those skilled in the art that other PIs, such as other UV-PIs and visible PIs, may also be used in accordance with aspects of the present invention.

Bioactive factors, such as adhesion ligands, growth factors, and cytokines, may be incorporated into the scaffold during the photocrosslinking process by including them in the polymer solution. These bioactive factors may be attached to the scaffold during the photocrosslinking process through functional groups attached to the factors, or may simply be trapped within the hydrogel during the process. The bioactive factors are preferably incorporated at a concentration effective to elicit the desired biological response.

Cells may be included in the polymer solution prior to the photocrosslinking process, thereby being homogeneously seeded within the scaffold following photocrosslinking of the hydrogel (or seeded into the scaffold after construction). The cell density may be wide-ranging depending on the particular application for which the scaffold will be used, but will typically not be more than about $50 \times 10^6$ cells/ml in the polymer solution.

In accordance with one aspect of the present invention, a complete TE cytocompatible hydrogel implant or construct was fabricated by first creating a desired nerve regeneration conduit computer-aided design (CAD) drawing. The design is saved in a standard transform language (STL) file format and imported in SL machine-specific software to create SL vector files or SL machine command files. Contemporaneously, hydrogel and PI selection occurs depending on the desired design criteria. A solution is prepared combining the hydrogel in distilled water and PI. Optionally, the solution may incorporate additives including, for example, bioactive agents, live cells, other chemicals, devices for implantation or any combination thereof. The solution may undergo several characterization tests including, for example, tests for evaluating mechanical, photo-chemical and cytocompatibility properties. After the initial design and testing phases are complete, the SL process may begin. After initialization of the SL machine, including laser power adjustment, SL machine-specific parameter determination, the hydrogel receptacle (or other existing receptacle), is placed at a desired height on the building platform. After determining the receptacle and solution volume required for a desired build layer thickness, the build process begins. Keeping in mind that build layer thickness may be varied as the build process continues, certain material volumes and machine parameters may need to be altered.

For example, to begin the building phase, an initial amount of solution is added into the receptacle, either by hand or by way of an automated system free of human intervention (or alternatively, the solution is contained in a fixed material vat similar to those found in existing commercial systems). Part building begins in accordance with the layer specific build file or machine command file using a machine adapted to perform SL including, for example, the SL machine schematically depicted in FIG. 3 without the optional glass slide. As each hydrogel construct layer is complete, the platform is traversed vertically a distance equal to the desired build layer thickness (which can be varied throughout the build).

In accordance with a preferred embodiment of the present invention, each hydrogel construct layer (or portion of a layer) may be fabricated to reflect a certain characteristic. As mentioned earlier, unique characteristics, such as hydrogel thickness or cure depth, vary widely as a function of PI type and concentration, energy dosage and polymer concentration in the hydrogel solution as also demonstrated in the later-described example. Thus, by changing PI type, PI concentration, polymer type, polymer concentration, solution type or solution concentration or energy dosage, the hydrogel solution generally exhibits a unique characteristic. Accordingly, in a preferred embodiment, although the entire hydrogel construct may be made of essentially the same material, distinct construct layers (or a portion of a layer), for example, exhibit unique physical and biological characteristics depending on the altered characteristics of the hydrogel solution used to fabricate that particular construct layer (or portion of a layer). Alternatively, it may be desired to build a layer (or a portion of a part layer) within or across the current part layer with altogether different materials. Keeping in mind that each layer may be built in a number of different configurations including, for example, partial layers, layers built in any one dimension or in multiple dimensions and cross-layers built between layers in any dimensions, a preferred embodiment of the present invention provides a system of fabricating virtually endless combinations of single material and multi-material hydrogel constructs, allowing different parts of the same hydrogel construct to exhibit a desired characteristic.

Figure 3:
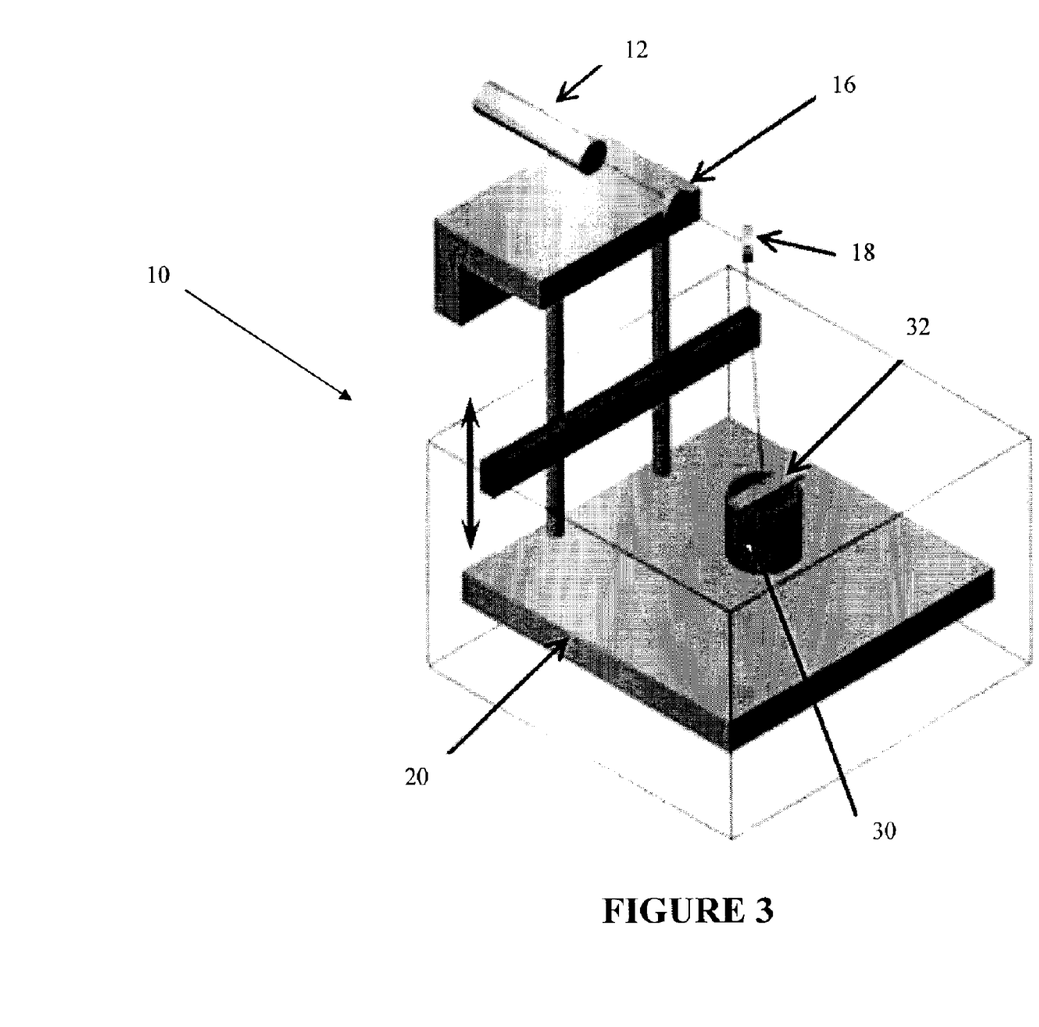
FIG. 3 illustrates a preferred working environment for building hydrogel construct with a typical SL machine (shown with an optional glass slide for measuring gel thickness)

As each part layer is completed, solution is added or removed accordingly to or from, respectively, from the receptacle to accommodate variable build layers (or portions of a build layer) and layer thickness (or thickness of a portion of a layer), using a receptacle fill/remove system (or alternatively, the platform could be traversed down into a single vat of material). The preferred building process is repeated using the build or machine command file until the part is complete. Finally, after removing all of the solution, the subject part is separated from the receptacle (or, alternatively the subject part is separated from an existing build platform or from an optional build platform such as a glass slide as seen in FIG. 3), the subject part is cleaned, optionally undergoes a finishing process that may include cutting or trimming the hydrogel construct, rinsing with a cytocompatible solution, and finally inspected for quality control. Accordingly, a completed TE hydrogel implant is cytocompatible and fabricated using SL. TE hydrogel implants additionally may promote, for example, adipose tissue population and growth (or nerve regeneration or guided angiogenesis and ultimately vasculogenesis).

Although the below-described example primarily references PEG, it should be understood by those skilled in the art that other hydrogels may also be used in accordance with the present invention. For example, a natural polymer, synthetic polymer or some combination thereof may also be used. Natural polymer hydrogels include polymers such as anionic polymers (for example, hyaluronic acid, alginic acid, pectin, carrageenan, chondroitin sulfate, dextran sulfate), cationic polymers (for example, chitosan and polylysine), amphipathic polymers (such as collagen, gelatin, carboxymethyl chitin and fibrin) and neutral polymers (for example, dextran, agarose and pullulan) and their derivatives.

Synthetic polymer hydrogels, on the other hand, include, for example, polymers such as polyesters: poly(ethylene glycol)-poly(lactic acid)-poly(ethylene glycol); poly(ethylene glycol)-poly(lactic-co-glycolic acid)-poly(ethylene glycol); poly(ethylene glycol)-polycaprolactone-poly(ethylene glycol); poly(lactic acid)-poly(ethylene glycol)-poly(lactic acid); poly(hydroxyl butyrate); poly(propylene fumerate-co-ethylene glycol)±acrylate end groups; and poly(poly(ethylene glycol)/poly(butylene oxide)terephthalate).

Synthetic polymer hydrogels may include, for example, other polymers such as: poly(ethylene glycol)-bis-(poly(lactic acid)-acrylate); poly(ethylene glycol)±cyclodextrins; poly(ethylene glycol)-g-poly(acrylamide-co-Vamine); polyacrylamide; poly(N-isopropyl acrylamide-co-acrylic acid); poly(N-isopropyl acrylamide-co-ethyl methacrylate); poly(vinyl acetate)/poly(vinyl alcohol); poly(N-vinyl pyrrolidone); poly(methyl methacrylate-co-hydroxyethyl methacrylate); poly(acrylonitrile-co-allyl sulfonate); poly(biscarboxy-phenoxy-phosphazene); and poly(glucosylethyl methacrylate-sulfate).

Combinations of natural and synthetic polymer hydrogels may include polymers such as poly(polyethylene glycol-co-peptides), alginate g-(polyethylene oxide-polypropylene oxide-polyethylene oxide), poly(polylactic-co-glycolic acid-co-serine), collagen-acrylate, alginate-acrylate, poly(hydroxyethly methacyrlate-g-peptide), poly(hydroxyethyl methacyrlate/Matrigel®) and hyraluronic acid-g-N-isopropyl acrylamide).

The SL materials used in accordance with a preferred embodiment of the present invention may be rigid, semi-rigid, liquid (may be encapsulated liquid) or gas (trapped gases). There are numerous examples of curable fluid media 24 suitable for use with aspects of the present invention. Examples of curable fluid media 24 or materials that may be incorporated into the curable fluid media 24 include SL resins known in the art, hydrogels, bioactive ingredients, cells, imbedded devices or materials, photopolymer resins and powdered materials. Some types of powdered materials may be converted from a fluid-like medium to a cohesive cross-section by processes, such as melting and solidification.

In addition, in accordance with a preferred embodiment of the present invention, multi-colored manufacturing may be accomplished by mixing pigments, fluorescing particles, paints, dyes and/or other color media into the curable fluid medium 24, thereby facilitating the manufacture of multi-colored prototypes and models. Similarly, other materials may, optionally, be mixed into the fluid medium 24 to alter the strength, thermal, mechanical, optical, electrical, functional and/or biofunctional properties thereby facilitating the manufacture of multi-functional, multi-material, multi-colored, multi-element and/or implantable prototypes, models and finished products. The present invention thus facilitates using SL technology to aid in manufacturing of parts in an endless number of materials and colors. The present invention also facilitates manipulating certain materials to exhibit altered properties at select locations during the building stage.

Example

Poly(ethylene glycol) (PEG) is an example of a synthetic hydrogel material which is cytocompatible and potentially has important uses in tissue regeneration. PEG is generally non-toxic, non-immunogenic and can be easily cleared from the body. In addition, PEG is water soluble and can be easily modified with photoreactive and crosslinkable groups like acrylates or methacrylates. Thus, PEG is ideal for creating photocrosslinkable hydrogel tissue scaffolds. The systems and methods in accordance with an aspect of the present invention make possible, for example, successful fabrication of 3D PEG-based scaffolds using SL.

Generally, it was found that hydrogel thicknesses vary at select energy dosages for different scan speeds of the SL machine's UV scanning system. In fact, hydrogel thickness was found to be a strong function of PI type and concentration, energy dosage and PEG-dimethacrylate (PEG-dma) concentration (for a molecular weight, $M_w$, of 1000 PEG-dma commercially available), especially at the low PI concentrations required for implantation. Hydrogel thickness curves demonstrate LM for two construct geometries where different layer thicknesses were required to successfully fabricate the constructs. Thus, an aspect of the present invention demonstrates, for example, the effective use of SL as a processing technique for complex cytocompatible 3D tissue scaffolds. In addition, other aspects of the present invention address, for example, practical considerations associated with the use of hydrogels in LM.

Figure 2:
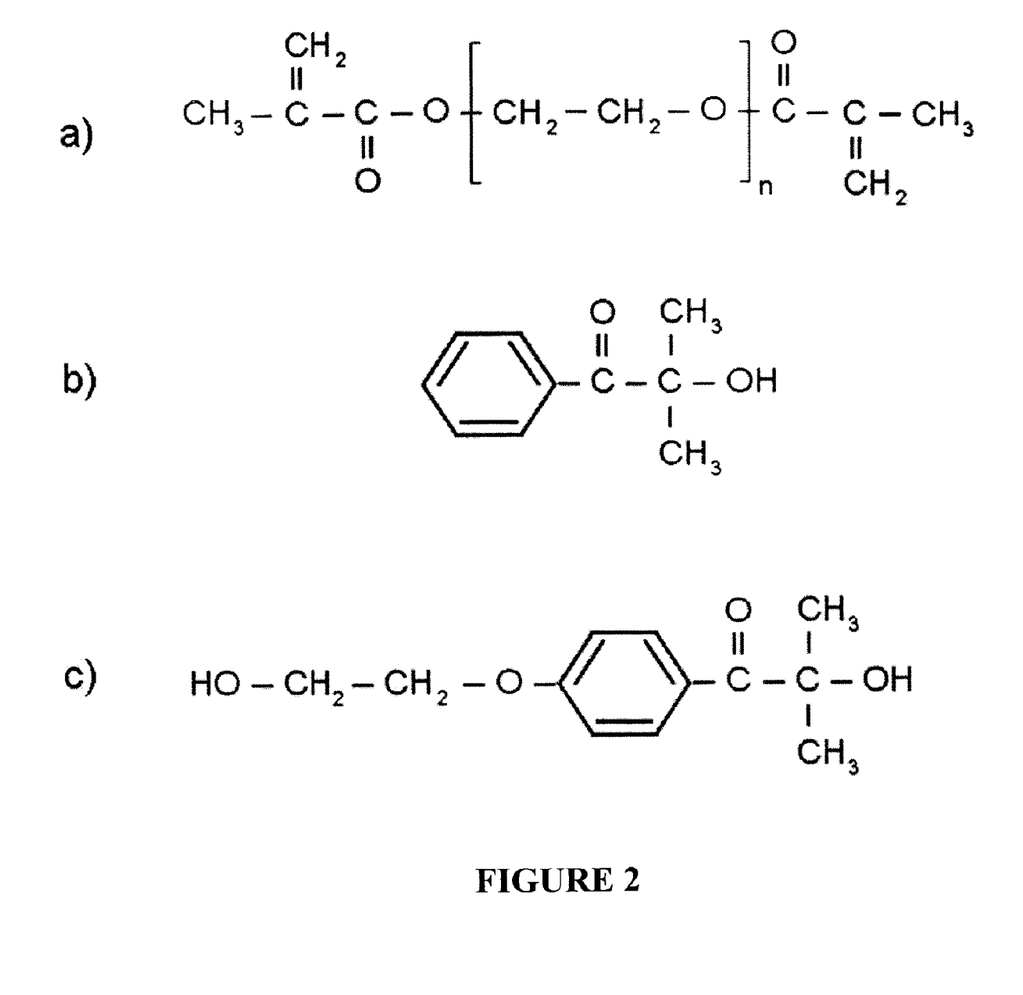

In accordance with an aspect of the present invention, PEG-dma $M_w$ 1000 was used to prepare two solutions with different concentrations (20% and 30% w/v) in distilled water. Aliquot portions were separated from these solutions, and different concentrations of two PIs were added to the portions. The PIs used in this instance were Sarcure1121 or HMPP (2-hydroxy-2-methyl-1phenyl-1-propanone) and Irgacure 2959 or I-2959 (2-hydroxy-1-[4-(2-hydroxehtoxy) phenyl]-2-methyl-1-propanone). The chemical structures of the PEG-dma and the two PIs used in this example are shown in FIGS. 2A, 2B and 2C, respectively.

In order to obtain viable hydrogel thickness curves, the movable platform 20 of the SL machine 10 was set a fixed height and fitted with a laser 12, specifically a He—Cd laser (325 nm) as seen in, for example, FIG. 3. The PEG-dma solution with PI was pipetted inside a flat-top cylindrical container 30 and filled to the rim. A glass slide 32 was placed on top of the container 30 and in contact with the PEG-dma solution. The glass slide 32 acts as a substrate for hydrogel attachment and facilitates the thickness measurements. It was determined that the glass slide 32 filters approximately 18% of the laser 12 power.

The cylindrical container 30 with the glass slide 32 was placed on the center of the platform 20 as depicted in FIG. 3. At the test height of the platform 20, the laser 12 was circular with a diameter of approximately 250-micrometers. The samples were cured by writing a vector pattern through the glass slide 32 and into the PEG-dma container 30 at different energy doses. FIG. 4C, for example, illustrates the vector file of the actual laser beam trace on laser burn paper. A preferred laser vector pattern 36 used to determine hydrogel thicknesses in accordance with an aspect of the present invention. The pattern 36, in this example, consisted of a series of nineteen parallel lines approximately 250 micrometers wide (the laser beam diameter) and 7.62 mm long, spaced approximately 355-micrometers apart.

The laser 12 drew each line in the pattern 36 twice and the energy dosage was varied by changing the SL machine 10 parameters that control the scan speed of the laser 12. After polymerization, the glass slide 32 was lifted off of the container 34 with the polymerized hydrogel attached to the slide. The cured hydrogels were rinsed with distilled water to remove any unreacted polymer and then measured with, for example, a caliper. This procedure was repeated for all hydrogel thickness measurements. Four sample hydrogels were cured for the PEG-dma solutions with I-2959, and two sample gels were cured for the solutions with HMPP. It should be noted that the measured power of the He—Cd laser 12 (rated at 40 mW) at the fixed platform 20 height was 29.5 to 30.6 mW and 35.8 to 37.1 mW with and without the glass slide 32, respectively. The measured laser 12 powers with the glass slide 32 were used to determine the laser energies.

Figure 4A:
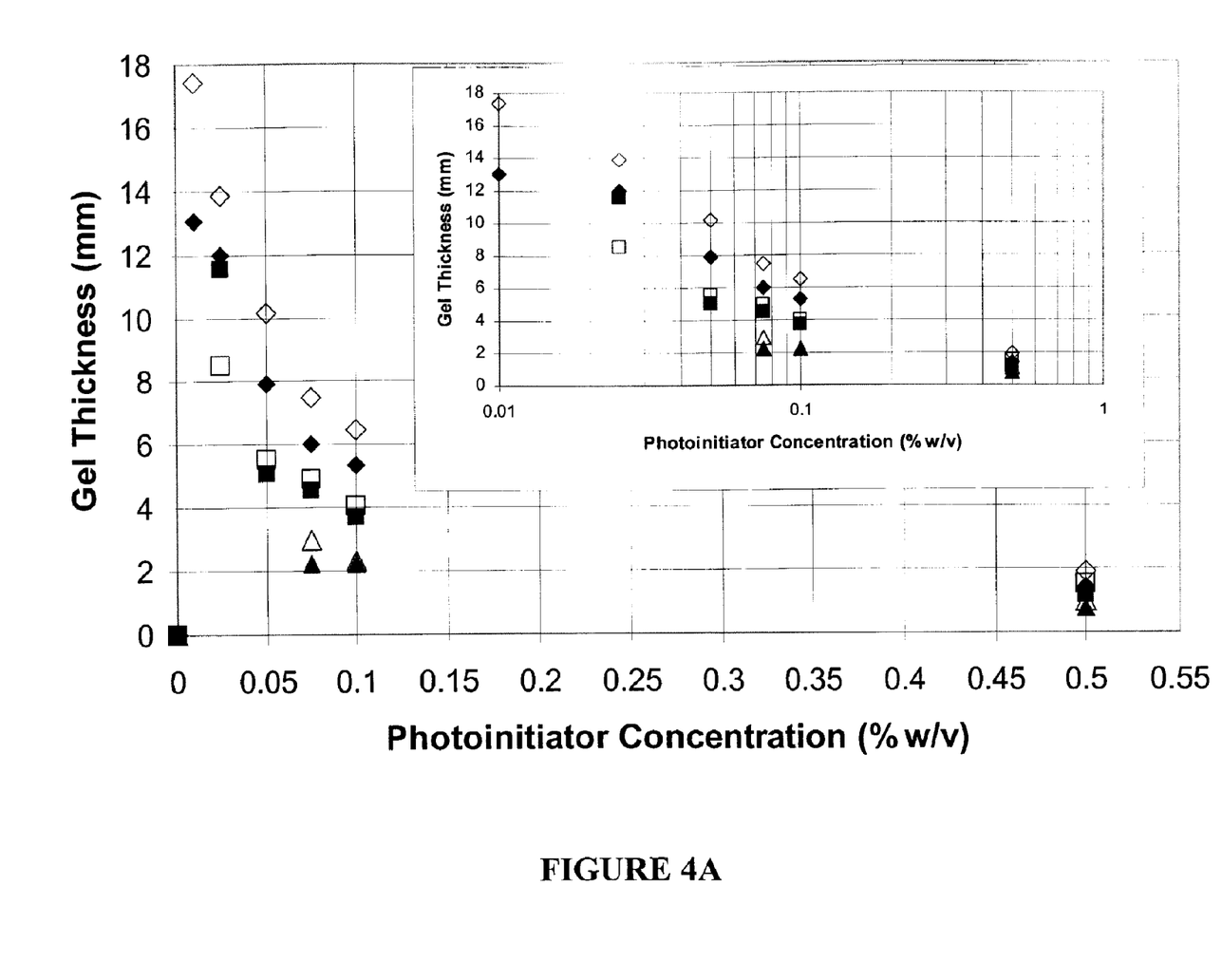
FIGS. 4A and 4B illustrate the cure depth or hydrogel thickness curves for preferred photoinitiators and hydrogel solutions used in an aspect of the present invention.
Figure 4B:
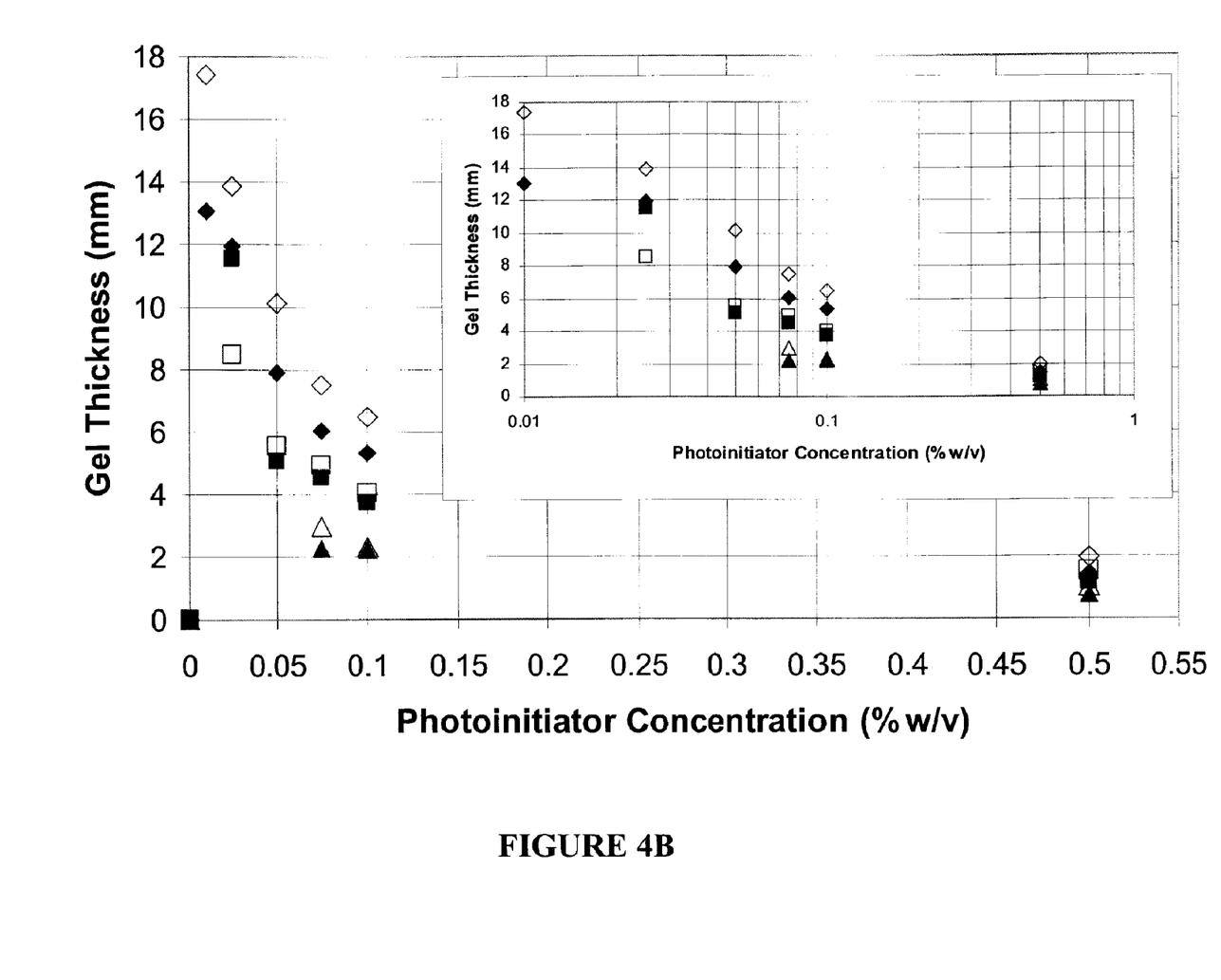
Figure 4C:
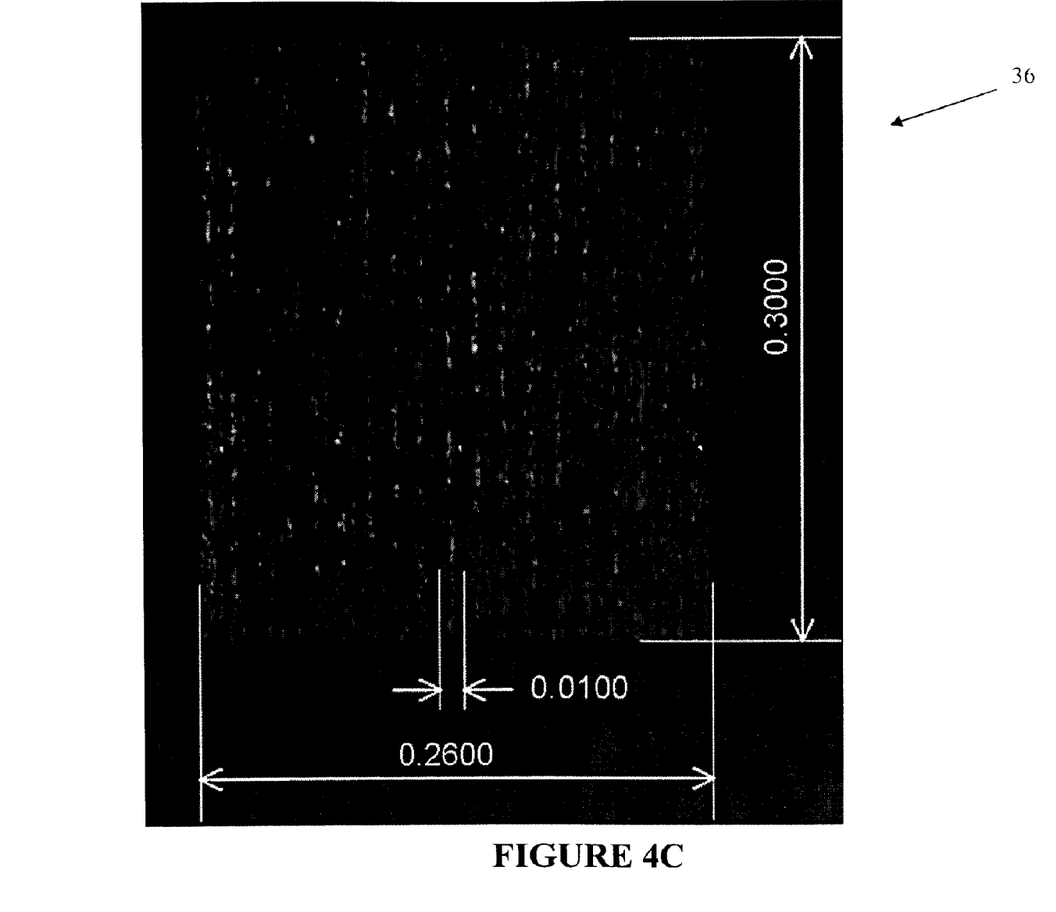
FIG. 4C illustrates a preferred laser vector pattern used to determine hydrogel thicknesses in accordance with an aspect of the present invention.

The resulting hydrogel thickness curves as a function of PI type and concentration and the energy dose are shown in FIGS. 4A and 4B, where FIG. 4A represents the gel thickness curve when I-2959 is used as a PI and FIG. 4B represents the same for HMPP. The three markers used in FIGS. 4A and 4B correspond to three different energy dosages. The diamond shape (♦) represents an energy level of 3.604 J/cm$^2$ or 0.258 IPS. The square shape (■) represents an energy level of 1.640 J/cm$^2$ or 0.567 IPS. The triangle shape (▲) represents an energy level of 0.586 J/cm$^2$ or 1.585 IPS.

FIGS. 4A and 4B also illustrate that there are significantly greater gel thicknesses achieved with HMPP when compared with I-2959 for a given PI concentration and energy dosage. It was further observed that higher polymer concentrations typically produce thicker hydrogels. Similarly, higher energy dosages generally produce thicker gels. Thus, the hydrogel thickness curves aid in prescribing layer thicknesses for fabricating complex 3D scaffolds. For example, the I-2959 affords polymerization of thin layers and therefore the fabrication in a layer-by layer fashion. On the other hand, HMPP may be used to successfully fabricate single layer "large" structures.

Figure 5:
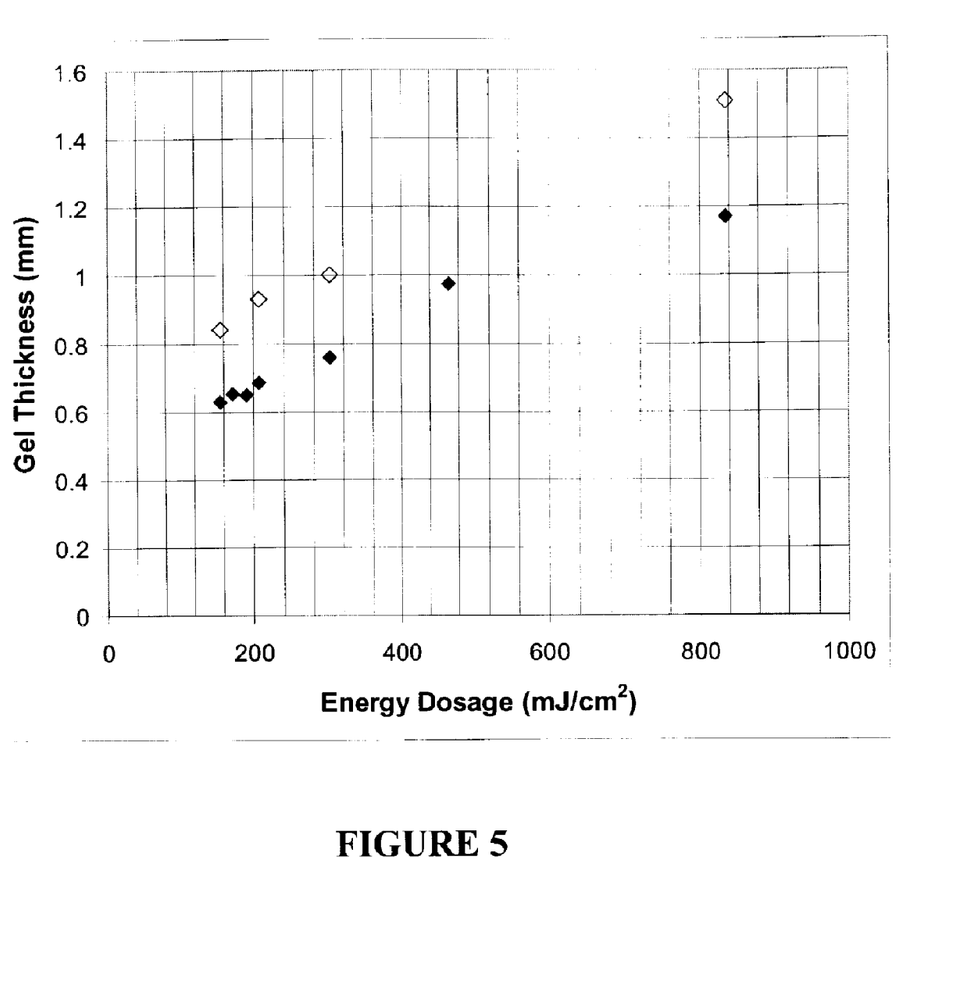
FIG. 5 illustrates the relationship between gel thickness and energy dosage for a preferred solution used in an aspect of the present invention.

FIG. 5 illustrates that there is a relationship between energy dosage and hydrogel thickness for PEG solutions with 0.5% (w/v) I-2959. The solid diamond markers (♦) correspond to 0.5% (w/v) of I-2959, while the hollow diamond markers (◊) correspond to 20% (w/v) PEG-dma in distilled water. Again, as seen in FIG. 5, for the two types of PIs tested, at low PI concentrations (<0.05%) and small energy dosages (fast scanning speeds) the hydrogels produced were thick and loosely crosslinked.

Figure 6:
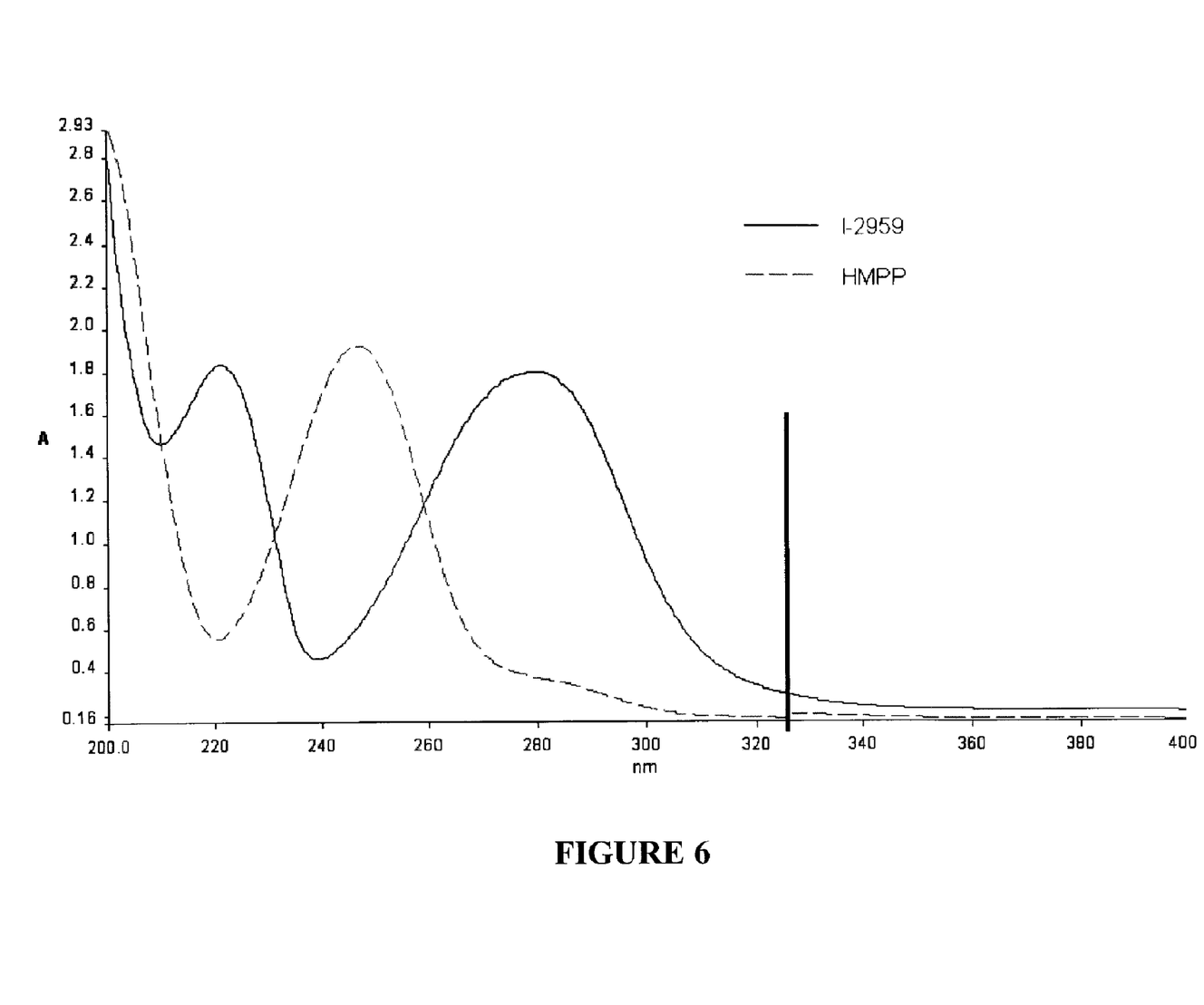
FIG. 6 depicts a typical UV-VIS absorption spectrum for preferred photoinitiators used in an aspect of the present invention.

FIG. 6 illustrates the UV-VIS absorption spectrum of the two PIs used in the gel thickness experiments and shows, for example, that the hydrogel thickness has a maximum at low PI concentrations and decreases asymptotically to a non-zero value as PI concentrations increase. Hydrogel thickness generally begins at zero for zero PI concentration, has a maximum at low PI concentrations, and decreases asymptotically to a non-zero value as PI concentration increases. Hydrogel thickness starts at zero due to the presence of polymerization inhibitors, including monomethyl ether hydroquinone (MEHQ) and butylated hydroxytoluene (BHT), added by the manufacturer in the PI. Measurement in the region between zero and the maximum gel thickness are not present here as the gel is loosely crosslinked at these PI concentrations and the measurements are highly uncertain (and thus, the maximum gel thickness presented here should not be viewed as an absolute maximum).

Figure 7:
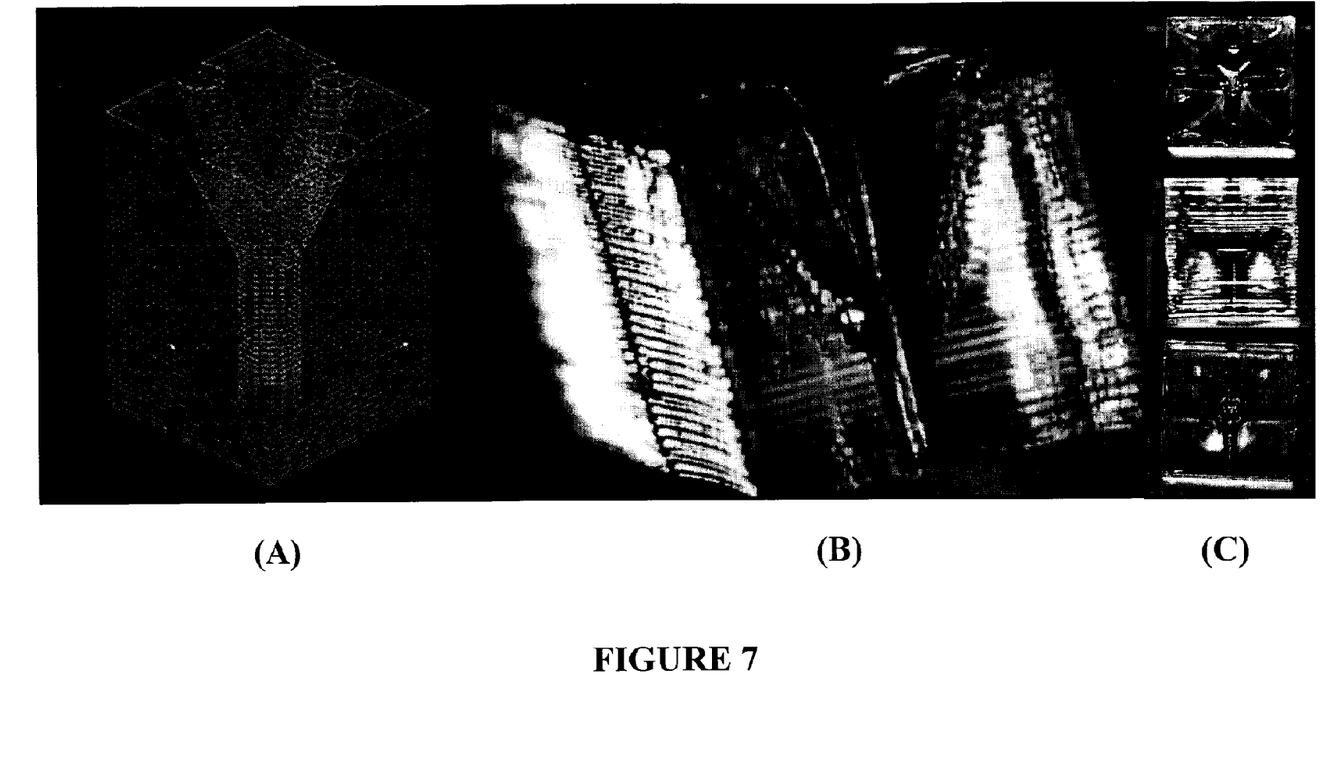
FIGS. 7A-C depict exemplary 3D tissue engineered scaffolds fabricated with I-2959 in accordance with an aspect of the present invention.
Figure 8:
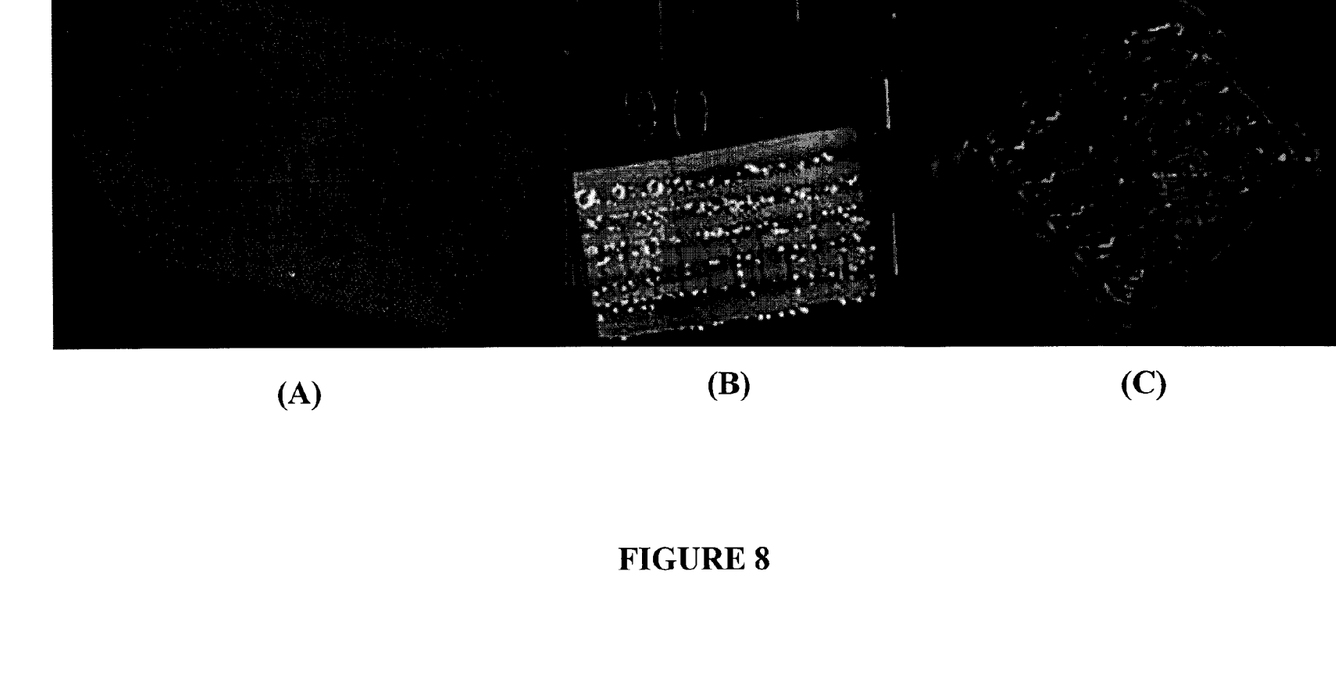
FIG. 8A depicts the vector file from the SL machine software depicting the path of the laser beam during the build process in accordance with an aspect of the present invention.
FIGS. 8B and 8C depict an exemplary 3D tissue engineered scaffolds fabricated with HMPP in accordance with an aspect of the present invention.
Figure 9:
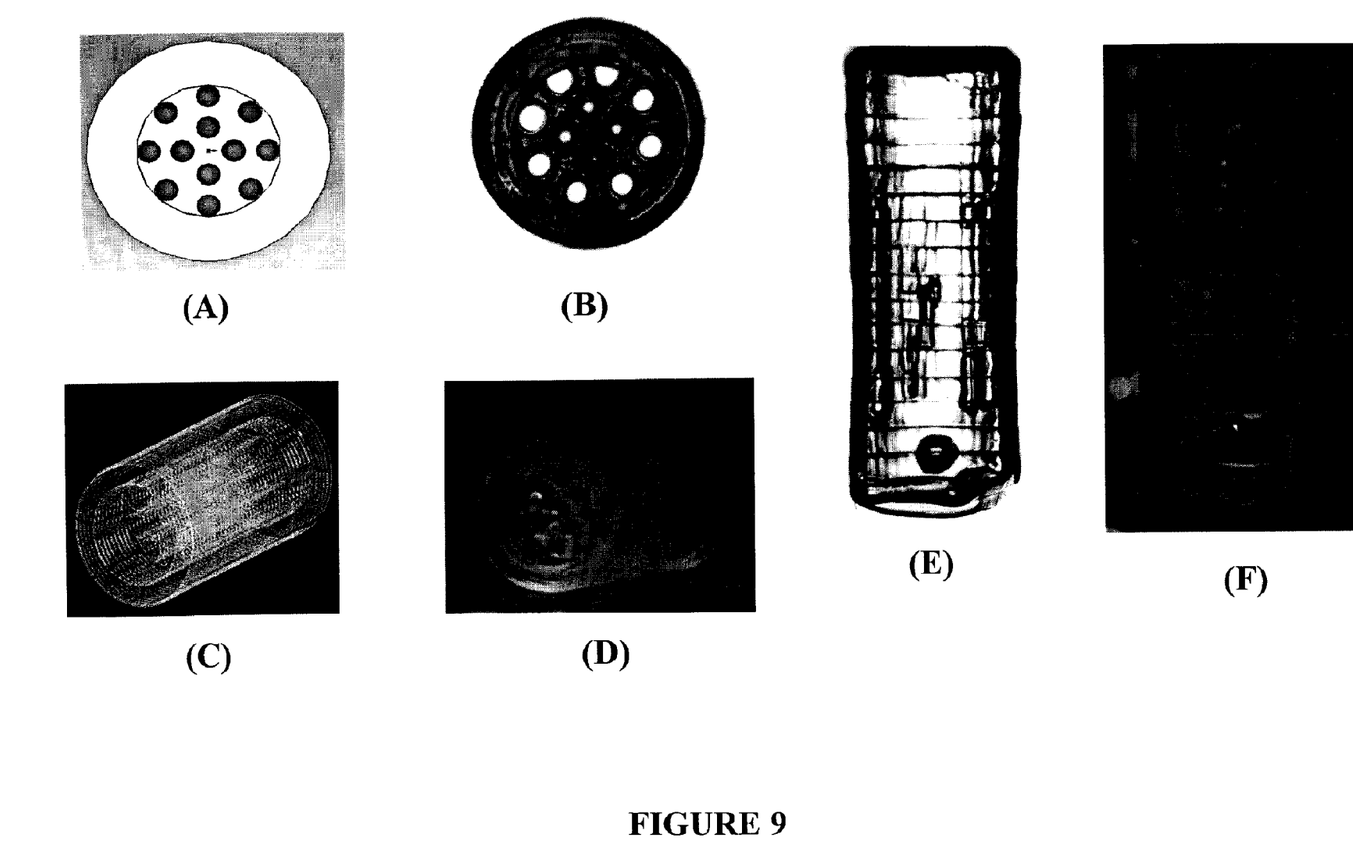
FIG. 9A depicts a CAD model of a preferred nerve guidance conduit.
FIG. 9B depicts the vector file from the SL machine software depicting the path of the laser beam during the build process in accordance with an aspect of the present invention.
FIGS. 9C-9F depict exemplary 3D multi-lumen nerve guidance conduits fabricated in accordance with a preferred embodiment of the present invention.

As mentioned earlier, I-2959 affords polymerization of thin layers and therefore the fabrication in a layer-by layer fashion, while HMPP may be used to successfully fabricate single layer "large" structures. Accordingly, a preferred embodiment of the present invention provides SL processing to fabricate cytocompatible parts such as those seen in FIGS. 7, 8 and 9. For example, FIG. 7A depicts the complex 3D structure with embedded 3D channel architecture encoded in a vector file. The vector file was in turn used to fabricate the scaffold depicted in FIGS. 7B and 7C using I-2959. As another example, FIG. 8A depicts the relatively simple structure with multiple straight channels encoded in a vector file. This vector file was used to fabricate the scaffold in one layer using HMPP as in FIGS. 8B and 8C.

FIGS. 9A-9F depict other examples of multi-lumen and multi-layered nerve guidance conduits which may be built in accordance with one aspect of the present invention. FIG. 9A depicts a CAD model of a preferred nerve guidance conduit while FIG. 9B depicts the vector file from the SL machine software depicting the path of the laser beam during the build process in accordance with an aspect of the present invention; and FIGS. 9C-9F depict exemplary 3D multi-lumen nerve guidance conduits fabricated in accordance with a preferred embodiment of the present invention.

It should be understood by those skilled in the art that there are numerous other shapes, sizes and configurations of tissue scaffolds and nerve guide conduits, for example, which may be fabricated using a preferred embodiment of the present invention. Although preferred embodiments of the present invention have been described in detail, it will be understood by those skilled in the art that various modifications can be made therein without departing from the spirit and scope of the invention as set forth in the appended claims.

What is claimed is:

1. A method of fabricating a hydrogel construct comprising:
    solidifying a first solution into a first hydrogel construct layer with a first energy dosage using stereolithography, the first solution comprising:
        a first hydrogel polymer having a first polymer concentration; and
        a first photoinitiator having a first photoinitiator concentration;
        where the first polymer concentration, first photoinitiator concentration, and first energy dosage are configured such that the cure depth of the first solution is less than or equal to two millimeters; and
    forming a second hydrogel construct layer using stereolithography.

2. The method of claim 1, wherein forming the second construct layer comprises solidifying a second solution into a second hydrogel construct layer, the second solution being different than the first solution.

3. The method of claim 1, wherein the first hydrogel polymer is a derivative of poly(ethylene glycol).

4. The method of claim 3, wherein the derivative of poly (ethylene glycol) has a weight average molecular weight between about 1,000 and about 10,000.

5. The method of claim 1, wherein the first hydrogel polymer is selected from the group consisting of natural polymers, synthetic polymers and any combination thereof.

6. The method of claim 1, wherein the first photoinitiator is a UV photoinitiator.

7. The method of claim 1, wherein the first photoinitiator is selected from the group consisting of: 2-hydroxy-2-methyl-1 phenyl-1-propanone, 2-hydroxy-1-[4-(2-hydroxyethoxy)

phenyl]-2-methyl-1-propanone, 2,2-dimethoxy-2-phenyl-acetophenone, and any combination thereof.

8. The method of claim 1, wherein the first photoinitiator is a visible light photoinitiator.

9. The method of claim 1, wherein the first solution further comprises one or more materials selected from the group consisting of: biocompatible media, water, a buffer, phosphate-buffered saline, cell culture media, and any combination thereof.

10. The method of claim 1, wherein the first solution has a pH of about 7.0 to about 7.8.

11. The method of claim 1, wherein the construct is cytocompatible.

12. The method of claim 1, wherein the construct is selected from the group consisting of a tissue scaffold, a single-lumen nerve guidance conduit, a multi-lumen nerve guidance conduit, an angiogenic structure, a scaffold for promoting adipose tissue population and growth, and any combination thereof.

13. The method of claim 1, wherein the first hydrogel construct layer comprises a first portion having a first thickness and a second portion having a second thickness.

14. The method of claim 1, wherein the thickness of the second hydrogel construct layer is different from the thickness of the first hydrogel construct layer.

15. The method of claim 1 further comprising a cross-layer disposed between the first hydrogel construct layer and the second hydrogel construct layer and further disposed in any dimension.

16. The method of claim 1, wherein the second hydrogel construct layer is a partial layer.

17. The method of claim 1, wherein fabricating the second hydrogel construct layer is accomplished using a second energy dosage.

18. The method of claim 2, wherein the second solution comprises a second hydrogel polymer that is different than the first hydrogel polymer.

19. The method of claim 2, wherein the second solution comprises the first hydrogel polymer having a second polymer concentration that is different than the first polymer concentration.

20. The method of claim 2, wherein the second solution comprises the first photoinitiator having a second photoinitiator concentration that is different than the first photoinitiator concentration.

21. The method of claim 1 further comprising cleaning the hydrogel construct.

22. The method of claim 1 further comprising curing/drying the hydrogel construct.

23. The method of claim 1 further comprising incorporating an additive into the first solution.

24. The method of claim 23, wherein the additive is selected from the group consisting of color altering, thermal property altering, electrical property altering, optical property altering, mechanical property altering, strength altering, function altering, biofunction altering additives and any combination thereof.

25. The method of claim 23, wherein the additive is selected from the group consisting of imbedded devices and imbedded materials, bioactive ingredients and cells, and any combination thereof.

* * * * *